US00PP31036P2

(12) United States Plant Patent
Hardiman

(10) Patent No.: US PP31,036 P2
(45) Date of Patent: Nov. 12, 2019

(54) CHERRY TREE NAMED 'KARA KING'

(50) Latin Name: *Prunus avium*
Varietal Denomination: Kara King

(71) Applicant: Brisky Canyon Co., Inc., East Wenatchee, WA (US)

(72) Inventor: Michael Lee Hardiman, East Wenatchee, WA (US)

(73) Assignee: Brisky Canyon Co., Inc., East Wenatchee, WA (US)

( * ) Notice: Subject to any disclaimer, the term of this patent is extended or adjusted under 35 U.S.C. 154(b) by 0 days.

(21) Appl. No.: 16/350,223

(22) Filed: Oct. 15, 2018

(51) Int. Cl.
*A01H 5/08* (2018.01)
*A01H 6/74* (2018.01)

(52) U.S. Cl.
USPC ..... Plt./181
CPC ..... *A01H 6/74* (2018.05); *A01H 5/08* (2013.01)

(58) Field of Classification Search
USPC ..... Plt./181
CPC ..... A01H 5/08; A01H 5/085
See application file for complete search history.

*Primary Examiner* — Kent L Bell
(74) *Attorney, Agent, or Firm* — Michelle Bos Legal LLC

(57) ABSTRACT

A new cherry tree named 'Kara King' distinguished primarily by its wide harvest window. Early fruit is yellow and light red, suitable for market as 'Rainier'-type cherry, while late-season fruit is dark red, suitable for market as a 'Bing'-type cherry. 'Kara King' is further distinguished by its large fruit size and high sugar content.

6 Drawing Sheets

Genus and species: *Prunus avium.*
Variety denomination: 'Kara King'.

BACKGROUND AND SUMMARY OF THE VARIETY

'Kara King' is a new sweet cherry tree discovered in 2004 in a 'Bing' (not patented) cherry orchard near East Wenatchee, Wash. 'Kara King' originated as a chance seedling of unknown parentage; 'Bing' and 'Rainier' (not patented) cherry trees planted nearby are possible parents. In 2005, scionwood cuttings of the seedling were budded on 'Mazzard' rootstock (not patented) near Quincy, Wash., to produce test trees for further observation. The test trees were planted in 2007 near Mattawa, Wash. The 'Kara King' cherry tree has been found to exhibit its distinctive characteristics through successive asexually propagated generations.

'Kara King' is distinguished primarily by its wide harvest window. Early fruit is yellow and light red, suitable for market as 'Rainier'-type cherry, while late-season fruit is dark red, suitable for market as a 'Bing'-type cherry. 'Kara King' is further distinguished by its large fruit size and high sugar content.

BRIEF DESCRIPTION OF THE PHOTOGRAPHS

Figure 1:
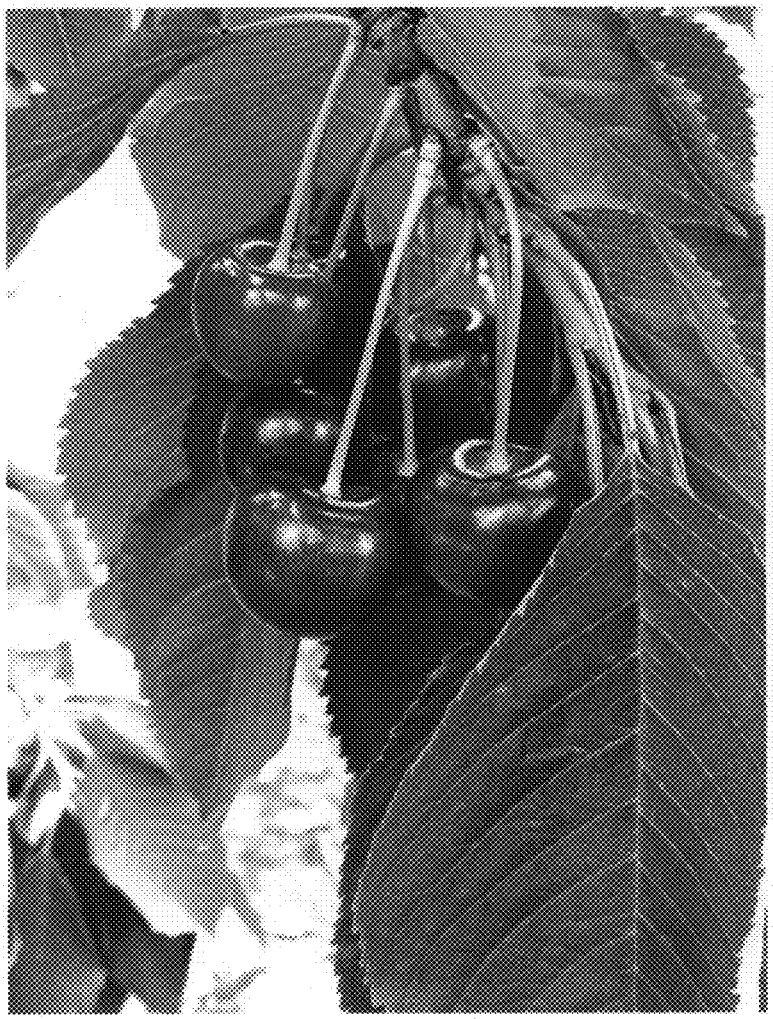
Figure 2:
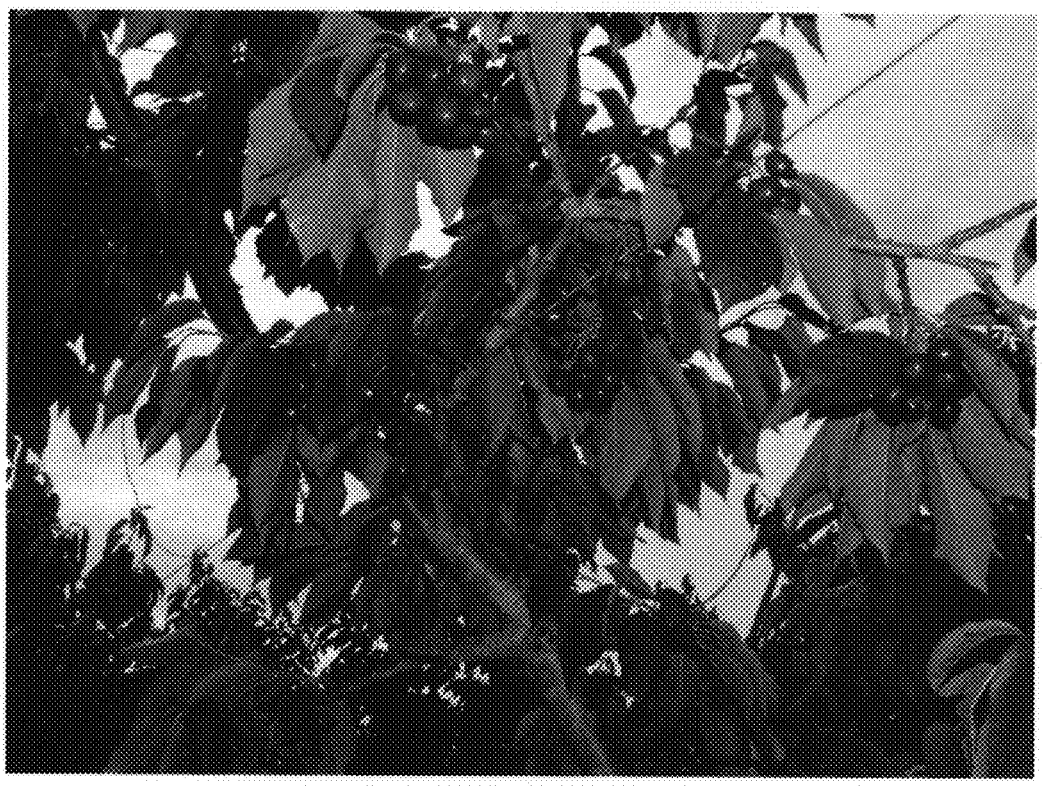
Figure 3:
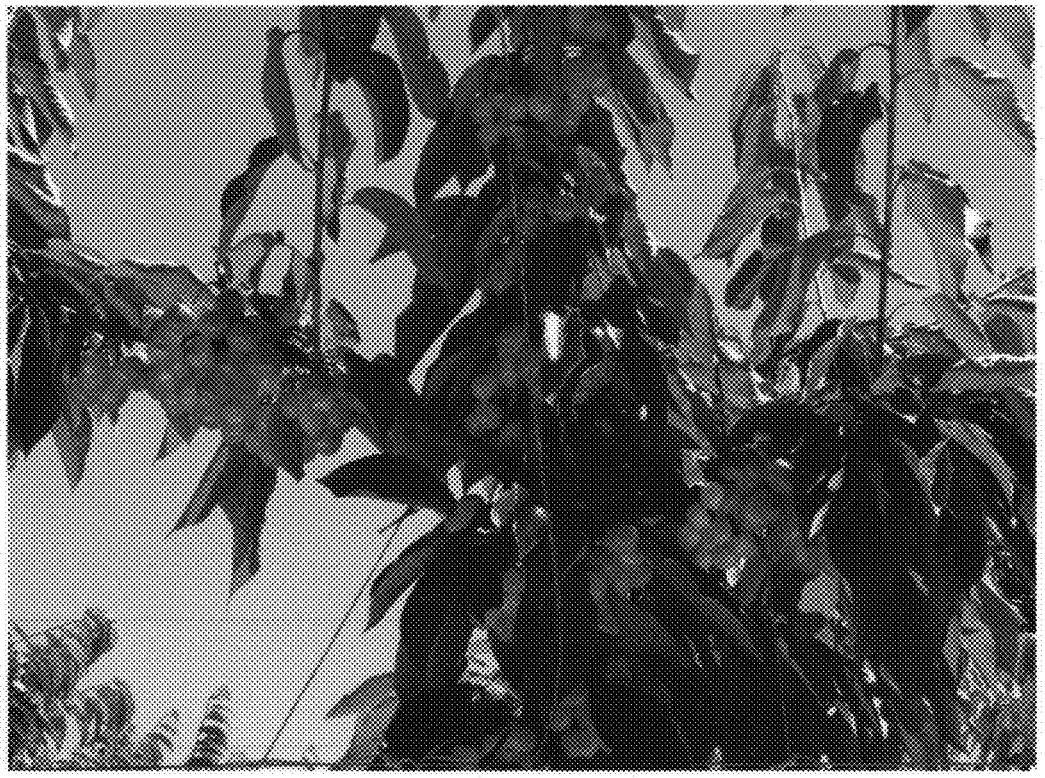
Figure 4:
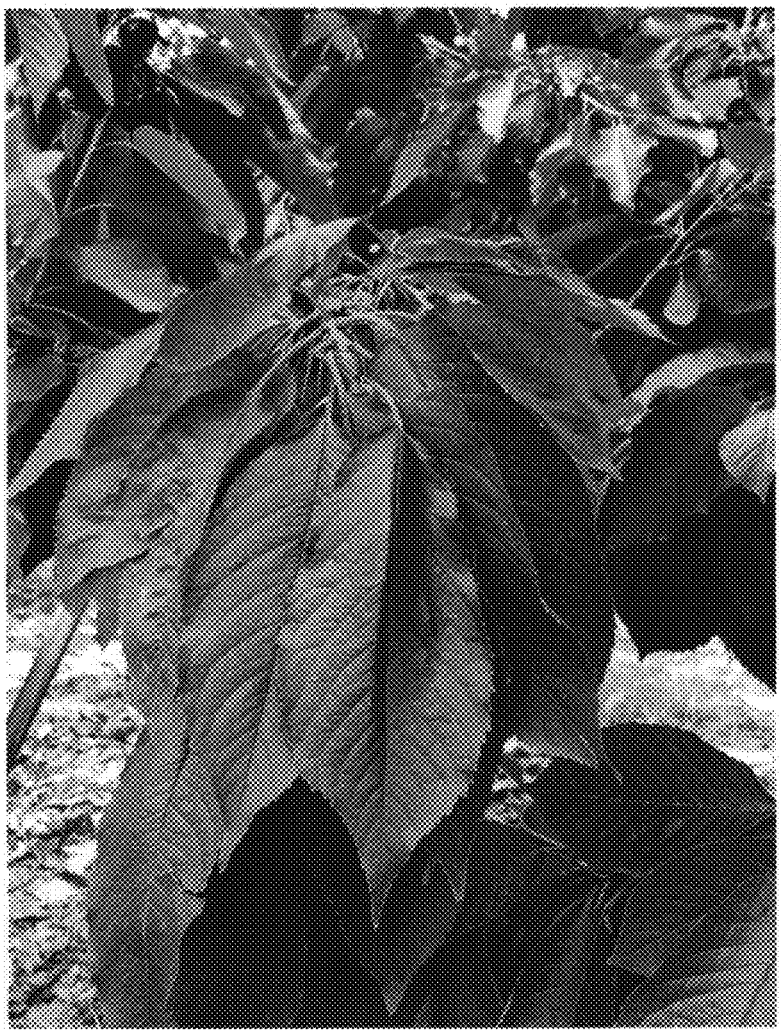
Figure 5:
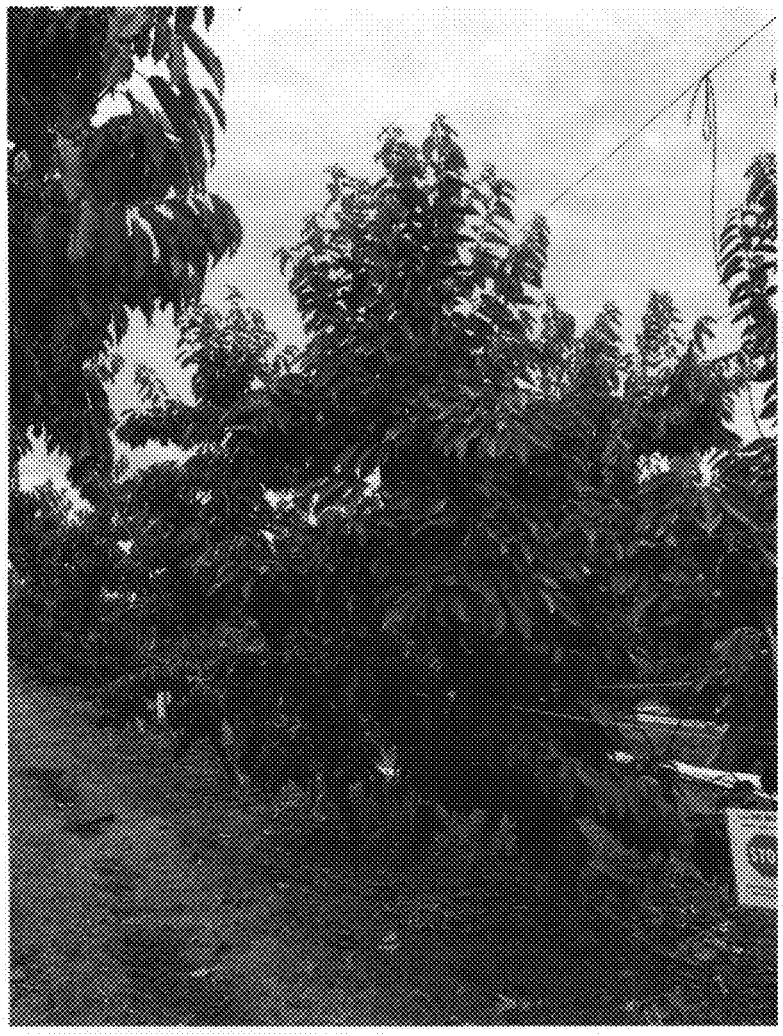

FIG. 1 shows the fruit of the variety;
FIG. 2 shows the fruit, leaves, and branches of the variety;
FIG. 3 shows the early yellow and light red fruit of the variety;
FIG. 4 shows the leaves of the variety;
FIG. 5 shows a tree of the variety; and
FIG. 6 shows a limb and blossoms of the variety.

Figure 6:
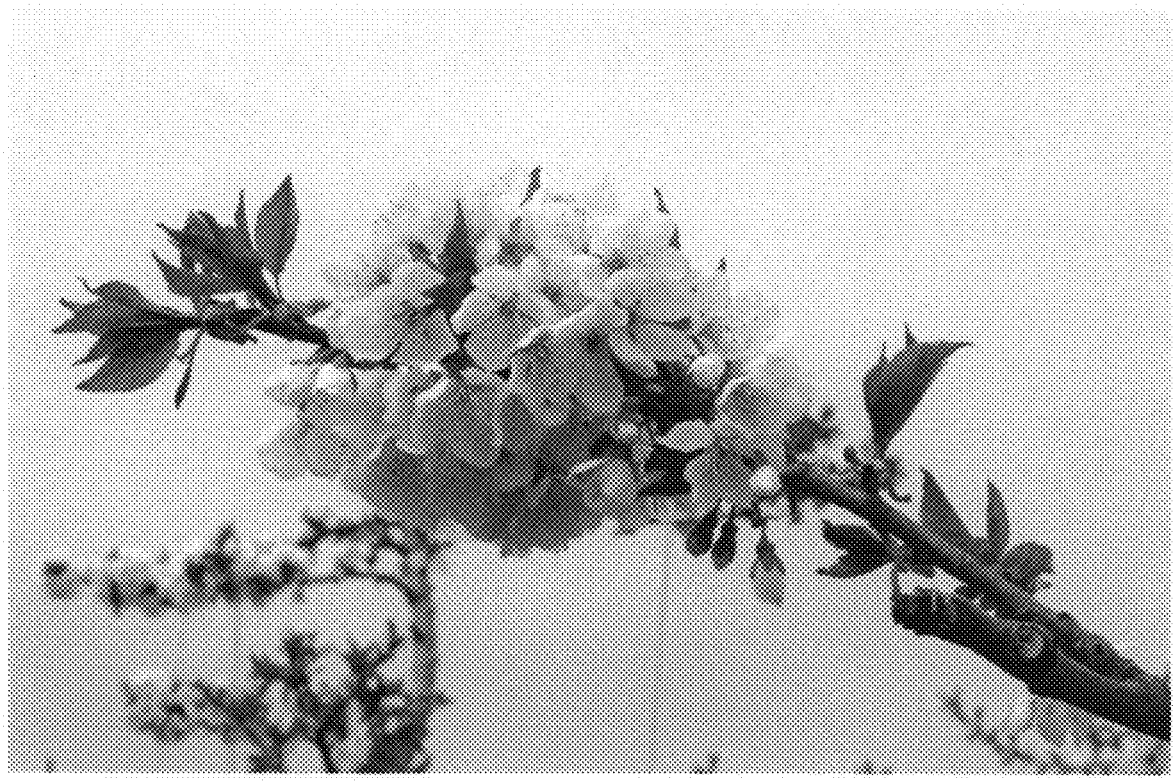

The photographs in FIGS. 1, 2, 4 and 5 were taken during June of 2018, and the photograph in FIG. 6 was taken on Apr. 18, 2018. The photograph in FIG. 3 was taken in June 2014. All photos are of trees planted in 2007 near Mattawa, Wash. The colors of the photographs may vary with lighting conditions. Color characteristics of the new variety should therefore be determined with reference to the observations described herein, rather than from the photographs alone.

DETAILED BOTANICAL DESCRIPTION

The following detailed botanical description is based on observations of second-generation trees of the variety, planted in 2007 and grown on 'Mazzard' rootstock (not patented) on a V-trellis system. Observations were recorded during the 2018 growing season near Mattawa, Wash. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Tree and branch colors are described with reference to The R.H.S. Colour Chart (Royal Horticultural Society, 6th edition 2015); all other colors are described with reference to the Munsell Book of Color.

Tree:

*Vigor.*—Vigorous.
*Habit, shape.*—Upright, spreading.
*Density.*—Dense.
*Height.*—4 m (trained on V-trellis).
*Spread.*—3 m (trained on V-trellis).
*Trunk diameter.*—14 cm at 30 cm above the ground.
*Bark texture.*—Smooth to medium.
*Bark color.*—Greyed-green 197D.
*Lenticel size.*—Length 5 mm to 10 mm, height 2 mm.
*Lenticel color.*—Greyed-orange 166A.

Branch (fruiting branches located at around 1 m above the graft union):
*Diameter.*—2 cm to 3 cm.
*Length.*—90 cm.
*Crotch angle.*—90° (trained on V-trellis).
*Bark color.*—Greyed-green 197D and greyed-orange 176B.
*Bark texture.*—Smooth.
*Lenticel.*—Length 1 mm to 2 mm; height 1 mm.
*Lenticel color.*—Greyed-orange 166A.
*Lenticel quantity.*—Scattered, averaging 1 per $cm^2$.

One year old shoot:
*Length.*—19 cm.
*Color.*—7.5 GY 6/4 (greenish tan).
*Pubescence.*—Glabrous.
*Diameter.*—4 mm.
*Internode length.*—4 cm.
*Lenticel size.*—Length 1 mm to 2 mm, height 0.5 mm.
*Lenticel color.*—7.5Y 3/4 (dark brown).
*Lenticel quantity.*—1 per $cm^2$.

Flower buds:
*Quantity per spur.*—3 to 15.
*Shape.*—Elongate, conic.
*Length.*—10 mm to 12 mm.
*Diameter.*—4 mm to 5 mm.
*Color.*—2.5 GY 6/8 (light green) two days prior to bloom.

Flowers:
*Diameter of fully open flower.*—30 mm.
*Depth of fully open flower.*—12 mm (not including pedicel).
*Relative position of petal margin.*—Slightly overlapping until fully open.
*Pedicel length.*—15 mm to 20 mm.
*Pedicel diameter.*—1.5 mm.
*Pedicel color.*—5 GY 5/10 (medium green).
*Number of flowers per cluster.*—2 to 3, occasionally 4.
*Date of first bloom.*—April 14 (2018).
*Date of full bloom.*—April 18 (2018).

Petals:
*Number per flower.*—5.
*Length.*—12 mm to 15 mm.
*Width.*—10 mm to 14 mm.
*Petal shape.*—Round obovate.
*Apex.*—Wavy, irregular; occasionally notched.
*Base.*—Acute.
*Margin.*—Smooth with some notching.
*Color of upper surface.*—White NN155D.
*Color of lower surface.*—White.

Pistil:
*Length.*—10 mm.
*Diameter.*—1 mm.
*Color.*—2.5 GY 9/2 (extremely pale green; almost white).

Stigma:
*Length.*—1.5 mm.
*Color.*—5 Y 8/4 (light yellowish brown).
*Position.*—Below anthers.

Style:
*Length.*—9 mm to 12 mm.
*Color.*—2.5 GY 8/4 (pale green).

Ovary:
*Length.*—4 mm.
*Diameter.*—2 mm.
*Color.*—2.5 GY 6/6 (light green).

Stamens:
*Quantity.*—25 to 30 per flower.
*Anther length.*—0.5 to 1 mm.
*Anther color.*—5Y 6/6 (yellow/brown).
*Filament size.*—Length 8 mm to 10 mm; diameter 0.5 mm.
*Presence of pollen.*—Abundant.
*Color of pollen.*—7.5 Y 7/10 (yellow).

Sepals:
*Quantity.*—5.
*Color.*—2.5 GY 7/6 (light green) (both surfaces).
*Shape.*—Obtuse to acute.
*Apex.*—Acute.
*Base.*—Broad.
*Margin.*—Smooth.
*Length.*—7 mm.
*Width.*—5 mm.

Leaves:
*Length.*—18 cm.
*Width.*—7 cm.
*Blade margin.*—Coarsely serrate.
*Leaf shape.*—Oblong lanceolate.
*Apex shape.*—Acuminate.
*Base shape.*—Oblate to tapering.
*Texture.*—Upper surface smooth, glabrous; underside dull with prominent veins.
*Attitude in relation to shoot.*—30 degrees to 60 degrees, with 60 degrees more prevalent.
*Color of upper surface.*—2.5 GY 5/4 (medium dark green).
*Color of lower surface.*—5 GY 6/8 (light-medium green).

Petiole:
*Length.*—3.5 cm to 5 cm.
*Diameter.*—2 mm to 3 mm.
*Color.*—2.5 GY 6/8 (light green).
*Glands.*—Oblong; length 3 mm, width 1 mm; Colored 10Y 7/6 (greenish tan).

Fruit:
*Quantity per cluster.*—2 to 3.
*Diameter.*—32 mm.
*Length.*—25 mm.
*Weight.*—1.1 g per fruit.
*General shape in profile.*—Reniform.
*Shape of stem end.*—Round cordate.
*Shape of pistil end.*—Round to flat.
*Depth of stalk cavity.*—2 mm.
*Diameter of stalk cavity.*—6 mm.
*Depth of suture.*—2 mm.
*Skin thickness.*—Thin to medium.
*Skin texture.*—Medium-smooth.
*Ground color.*—Ranges from yellow 5 Y 9/4 (June 10, see FIGS. 3) to 2.5 R 2/6 (deep purple red) to 5 R 2/4 (dark purple red) (June 21, see FIGS. 1 and 2).
*Overcolor.*—Light red (June 10, see FIG. 3) to not perceptible (June 21, see FIGS. 1 and 2); extremely glossy finish.
*Tendency to crack.*—None during dry weather; similar to 'Bing' in wet weather.

Stalk:
*Length.*—39 mm.
*Diameter.*—1.6 mm.
*Color.*—5 GY 5/6 (medium green).

Flesh:
*Flesh texture.*—Tender.

*Firmness*.—Very firm; typically 350 g/mm or higher.
*Fibers*.—Few small fibers.
*Aroma*.—Very slight.
*Flavor*.—Mildly flavored, well balanced; sweeter than 'Bing' but otherwise similar.
*Juiciness*.—Medium to juicy.
*Soluble solids*.—Early fruit 17 to 21° Brix; later fruit 21 to 23° Brix or more.
*Flesh color*.—10 RP 3/3 to 10 RP 3/6 (dark red purple).
*Juice color*.—10 RP 4/4 (dark purple pink).

Stone:

*Length*.—12 mm to 13 mm.
*Diameter*.—10 mm.
*Shape*.—Round.
*Color*.—5 Y 6/6 (medium yellow).
*Surface texture*.—Smooth.
*Adherence of flesh to stone*.—Semi-free.
*Tendency to split*.—None observed.

Harvest:

*Harvest date*.—June 5 to June 21 (2018).
*Number of picks*.—1.
*Harvest yield*.—22 kg to 27 kg.
*Bearing*.—Annual.
*Chilling requirement*.—Similar to 'Bing'.
*Cold hardiness*.—Hardy in area tested (North Central Washington, USDA Zone 5).
*Disease resistance/susceptibility*.—None noted; similar to 'Bing'.
*Market use*.—Fresh.
*Keeping quality*.—Good.
*Shipping quality*.—Good.

I claim:

1. A new and distinct cherry tree, substantially as illustrated and described herein.

* * * * *